United States Patent
Hill, III et al.

(10) Patent No.: US 6,972,016 B2
(45) Date of Patent: Dec. 6, 2005

(54) HELICALLY SHAPED ELECTROPHYSIOLOGY CATHETER

(75) Inventors: Richard E. Hill, III, Berkeley, CA (US); Alex L. Lim, Santa Clara, CA (US); Tim Huynh, Santa Clara, CA (US); Eric K. Y. Chan, Newark, CA (US)

(73) Assignee: CaRDiMa, Inc., Fremont, CA (US)

( * ) Notice: Subject to any disclaimer, the term of this patent is extended or adjusted under 35 U.S.C. 154(b) by 0 days.

(21) Appl. No.: 09/847,181

(22) Filed: May 1, 2001

(65) Prior Publication Data

US 2002/0165532 A1    Nov. 7, 2002

(51) Int. Cl.[7] .............................................. A61B 18/14
(52) U.S. Cl. ........................ 606/41; 607/99; 607/113; 607/122
(58) Field of Search ..................... 606/41, 49; 607/99, 607/113, 122

(56) References Cited

U.S. PATENT DOCUMENTS

| | | | |
|---|---|---|---|
| 6,325,797 B1 * | 12/2001 | Stewart et al. | 606/41 |
| 6,628,976 B1 * | 9/2003 | Fuimaono et al. | 600/374 |
| 2001/0020174 A1 * | 9/2001 | Koblish | 606/194 |
| 2002/0004631 A1 * | 1/2002 | Jenkins et al. | 606/41 |
| 2002/0062124 A1 * | 5/2002 | Keane | 606/41 |

* cited by examiner

*Primary Examiner*—Lee S. Cohen
(74) *Attorney, Agent, or Firm*—Edward J. Lynch; Duane Morris LLP (57) ABSTRACT

An electrophysiology (EP) device suitable for ablating tissue within a patient's body lumen. The EP device of the invention generally comprises an elongated shaft having a distal shaft section with a helical shape and at least one electrode on an exterior portion thereof. One aspect of the invention comprises a method of performing a medical procedure, such as treating a patient for atrial arrhythmia, by forming a lesion using an EP device embodying features of the invention.

26 Claims, 7 Drawing Sheets

HELICALLY SHAPED ELECTROPHYSIOLOGY CATHETER

BACKGROUND OF THE INVENTION

This invention generally relates to the treatment of cardiac arrhythmia and particularly atrial fibrillation and atrial flutter.

Atrial fibrillation is the disorganized depolarization of a patient's atrium with little or no effective atrial contraction. Prior methods for treating a patient's arrhythmia include the use of anti-arrhythmic drugs such as sodium and calcium channel blockers or drugs which reduce the Beta-adrenergic activity. Other methods include surgically sectioning the origin of the signals causing the arrhythmia or the conducting pathway for such signals. However, the surgical technique is quite traumatic and is unacceptable to a large number of patients. A more frequently used technique to terminate the arrhythmia involves destroying the heart tissue which causes the arrhythmia by ablative energy, e.g., applying a laser beam or high frequency electrical energy such as RF or microwave energy, to a desired arrhythmogenic site or pathway on the patient's endocardium. In the latter method, intravascular electrophysiological (EP) devices can be used to form lesions within a patient's atrial chamber to provide results similar to the surgical segregation techniques in terminating atrial fibrillation, but with significantly reduced trauma.

Typically, the EP device is advanced within a patient's vasculature and into a heart chamber, and a lesion is formed on the endocardium when RF electrical energy is emitted from electrodes of the device. RF ablation techniques produce lesions of a small area, so that several lesions are typically formed to completely ablate an area. A major problem of RF ablation techniques is forming a lesion of the requisite size, which completely ablates the area of interest but does not unnecessarily destroy surrounding healthy tissue.

What has been needed is an ablation device which allows for improved creation of lesions of a requisite shape. The present invention satisfies these and other needs.

SUMMARY OF THE INVENTION

This invention is directed to an electrophysiology (EP) device for ablating tissue within a patient's body lumen. The EP device of the invention generally comprises an elongated shaft having a distal shaft section with a helical shape and at least one electrode on an exterior portion thereof. One aspect of the invention comprises a method of performing a medical procedure, such as treating a patient for atrial arrhythmia, by forming a lesion using an EP device embodying features of the invention. The terminology helically shaped should be understood to refer to at least one turn having a distal portion of the turn longitudinally spaced from a proximal portion of the turn, at least when the helically shaped section is not in a reversibly stacked, longitudinally collapsed configuration.

In one embodiment, the helical shape of the distal shaft section is configured to conform to the inner diameter of a patient's body lumen, to form one or more lesions which extend around a wall defining the body lumen. Thus, the turns of the helical distal shaft section have an outer diameter which is not significantly smaller or significantly larger than the inner diameter of the body lumen at the desired site of the lesion. In a presently preferred embodiment, the diameter of the turns is substantially equal to the inner diameter of the body lumen, so that the turns contact the wall defining the body lumen without significantly expanding and injuring the body lumen wall.

In another embodiment, the distal shaft section has a proximal portion with a helical shape and a distal portion with a noncoiled shape, and at least one electrode on the distal shaft section. The noncoiled distal portion, which thus is not wound into circular or helically spiraled configuration, in one presently preferred embodiment has a substantially straight shape. The terminology "substantially straight" should be understood to mean a portion configured to extend in a line, although some minor variations in the shape of the portion may be present. In a presently preferred embodiment, electrodes for ablation, and optionally also for sensing and pacing, are on the helical proximal portion. In one embodiment, electrodes for sensing and/or pacing are provided on the noncoiled distal portion of the distal shaft section, which can be used to map electrical activity in the region of the electrodes, or to pace the electrical activity of a region of the patient's anatomy such as the patient's heart.

In a presently preferred embodiment, the EP device has a core member extending within the elongated shaft. The core member preferably has a helically shaped distal section to provide the helical shape to the distal shaft section of the EP catheter. The core member may be fixed within the shaft, or alternatively, slidably disposed therein. In the embodiment in which the core member is slidably disposed within the shaft, a variety of different core members may be provided allowing the physician to choose a core member comprising a particularly suitable size, shape or material. Thus, an EP device with a distal shaft section having a desired shape is provided by inserting a core member having the desired shape therein. The core member may be provided with one or more jackets, which may be electrically insulating, having a total thickness of preferably less than about 0.001 inch (0.025 mm).

The distal shaft section of the EP device is preferably reversibly deformable from the helically shaped configuration to a lower profile configuration for advancement within the patient's vasculature. In one embodiment, the EP device of the invention is slidably disposed in the lumen of a guiding catheter, so that the radial force of the guiding catheter against the device reversibly collapses the turns of the helically shaped distal section to smaller diameter turns which fit within the guiding catheter. In another embodiment, the turns of the helically shaped distal section are configured to reversibly collapse completely, so that the guiding catheter straightens the helically shaped distal section to a straight configuration. The EP device distal shaft section is thus constrained from assuming the expanded helical configuration until the device is displaced out a distal end of the guiding catheter.

The one or more electrodes on the helically shaped distal shaft section can be used as ablation electrodes to form a lesion from within a patient's body lumen when electrical energy, and preferably high frequency energy such as RF energy, is emitted therefrom. The ablation electrode(s) on the helically shaped distal shaft section may be a combination ablation and sensing electrode, which is capable of ablation and detection of electrical activity from within a lumen of the patient's body. In a presently preferred embodiment, the ablation electrode on the helically shaped distal shaft section is a helical coil for improved device flexibility, although other electrode designs are suitable including cylindrical bands, arcuate bands, ribbons or the like. A temperature sensor such as a thermocouple may be provided on the EP device. In one embodiment, the device includes one or more electrodes for mapping and/or pacing are provides on the shaft proximal and/or distal to the helically shaped section in addition to the electrodes on the helically shaped section. Preferably, the electrodes on the helically shaped distal shaft section are configured for unipolar use during ablation, and bipolar use during sensing, by use of a multiplexing switchbox. The sensing/pacing electrodes proximal and/or distal to the helically shaped section are preferably configured for bipolar use, but may be configured for unipolar mode use. In the unipolar sensing/pacing mode, a separate, return electrode which is not on the EP device shaft but which is in contact with the exterior surface of the patient's body is used.

In a method of the invention, the helically shaped distal shaft section of the EP device is placed at an ostium or within a body lumen at a desired location. The terminology "body lumen" should be understood to include a variety of structures in the body, including a blood vessel and a heart chamber. Typically, an EP device assembly comprising the EP device of the invention within a guiding catheter is advanced within a patient's body lumen to a desired location therein. The EP device distal shaft section is then deformed from the low profile configuration to the helical configuration by displacing the EP device relative to the guiding catheter so that the distal shaft section of the device extends at least in part outside of the guiding catheter lumen in the body lumen. The helically shaped distal shaft section of the device contacts a wall defining the body lumen or ostium. The electrodes are then used to detect electrical activity from within the body lumen to determine the desired site for forming a lesion. One or more of the electrodes on the helically shaped distal shaft section contact the wall defining the ostium or the inner surface of the body lumen, so that delivery of high frequency energy to the electrodes forms a lesion extending in whole or in part, one or more times, around the ostium or the inner surface of the body lumen. The lesion may be a helically shaped lesion extending spirally along a length of the body lumen, or may be one or more circular lesions. The helical shape of the distal shaft section is configured to provide lesions particularly suitable for treatment of atrial arrhythmia including atrial fibrillation or flutter. In one embodiment, a plurality of discontinuous lesions are formed, which thus limits or avoids the possible disadvantageous results, such as stenosis formation and spasms in the ablated region, which otherwise occur from a continuous lesion extending around the full circumference of the ostium or body lumen.

The EP device of the invention provides for improved lesion formation due to the ablation electrodes on the helically shaped distal section having at least one 360° turn. The helically shaped distal section allows for the formation of lesions extending in whole or in part around the inner surface of a patient's body lumen. The turns of the helically shaped distal shaft section can be moved closer together or further apart within the patient to provide the desired lesion pattern. Additionally, the device has a low profile configuration for advancement within the patient which self expands into the helically shaped configuration for easy of deployment within the patient. These and other advantages of the invention will become more apparent from the following detailed description and the accompanying exemplary drawings.

DETAILED DESCRIPTION OF THE INVENTION

Figures 1, 2:
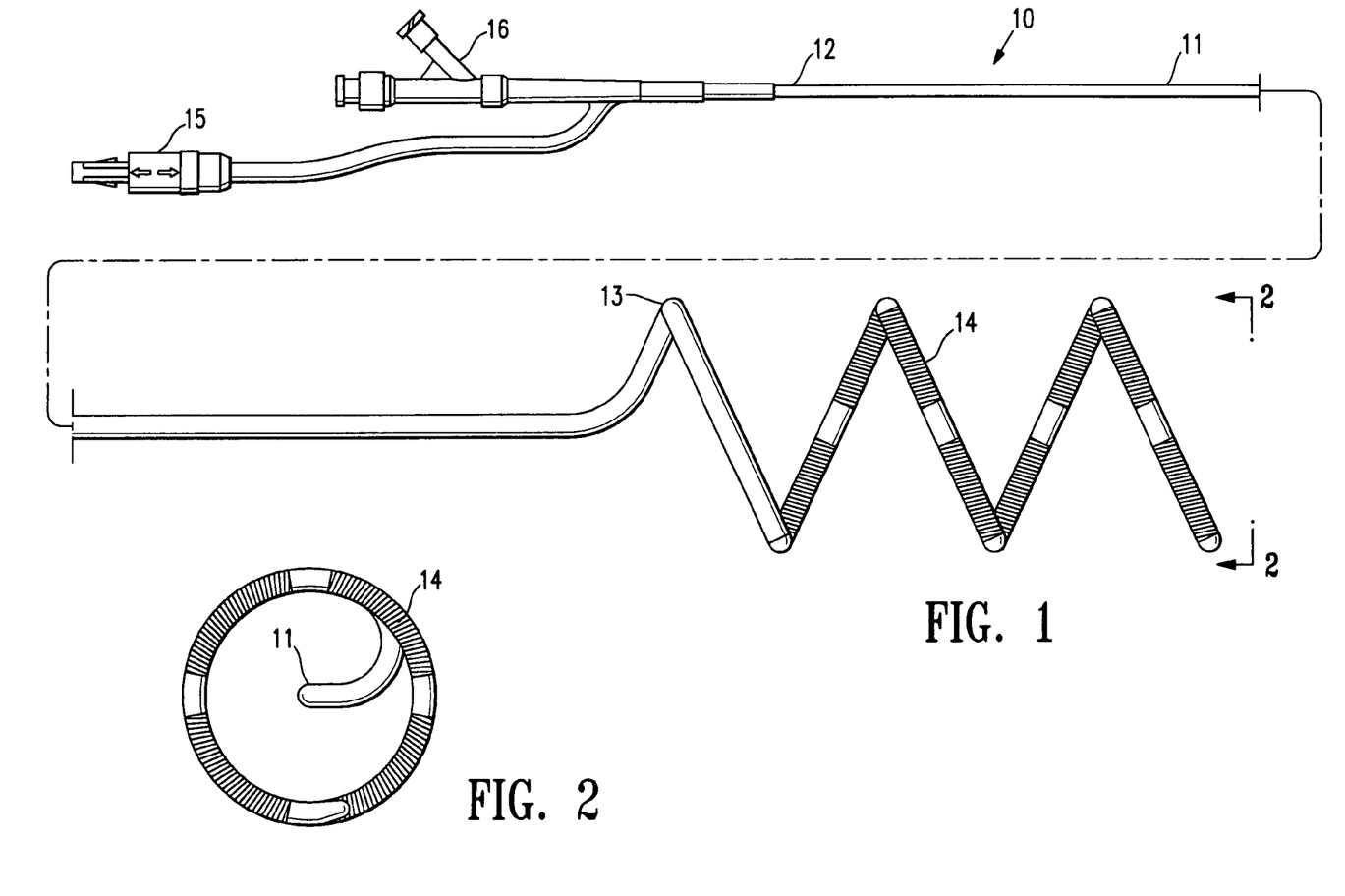
FIG. 1 is an elevational view of an EP device embodying features of the invention, having a helically shaped distal shaft section.
FIG. 2 is a transverse cross-sectional view of the EP device shown in FIG. 1, taken along the lines 2—2.

FIG. 1 illustrates one embodiment of the EP device 10 of the invention, generally comprising an elongated shaft 11 having a proximal shaft section 12, a helically shaped distal shaft section 13, and a plurality of electrodes 14 on the distal shaft section 13. An electrical connector 15 and an adapter 16 are on the proximal end of the device. FIG. 2 illustrates a transverse cross section of the distal end of the device 10 shown in FIG. 1, taken along lines 2—2.

Figure 3:
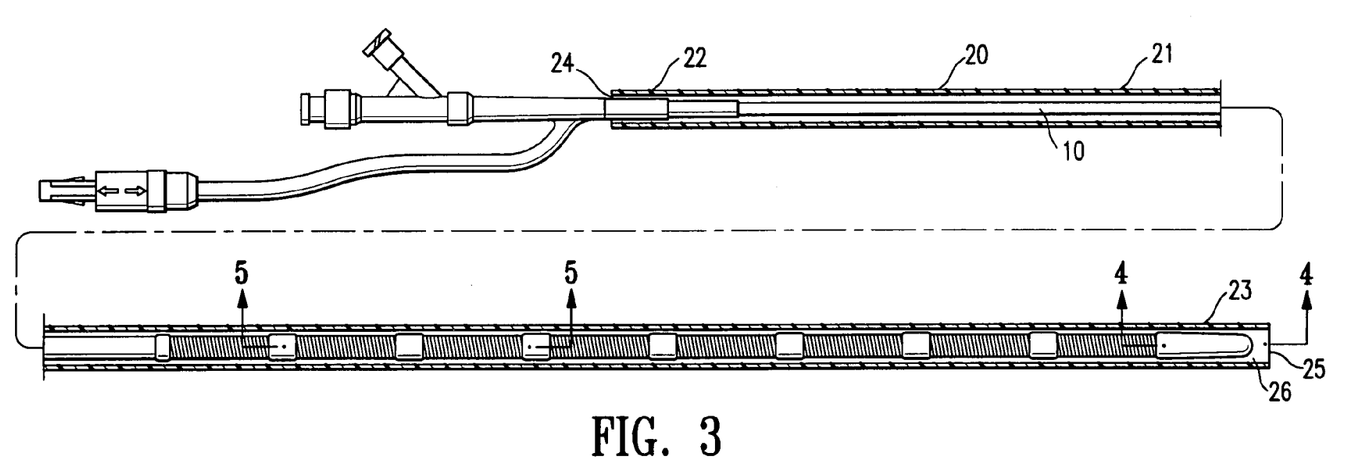
FIG. 3 is an elevational view, partially in section, of an EP device assembly embodying features of the invention, illustrating an EP device in a low profile configuration within a guiding catheter.

FIG. 3 illustrates the EP device 10 within a guiding catheter 20 for introduction and advancement within the patient. The guiding catheter generally comprises an elongated shaft 21 having a proximal end 22, a distal end 23, a port 24 in a proximal shaft section, a port 25 in a distal shaft section, and a lumen 26 extending within the shaft to the port in the distal shaft section. As illustrated in FIG. 3, the helically shaped distal shaft section of the EP device 10 is reversibly deformed from the helical configuration to a low profile configuration within the lumen 26 of the guiding catheter. In the embodiment illustrated in FIG. 3, with the EP device slidably disposed within guiding catheter lumen 26, the radial force of the guiding catheter 20 against the device reversibly straightens the helically shaped distal section to form a straight configuration. The helically shaped distal shaft section 13 is preferably self expanding, so that the EP device 10 can be advanced out the distal end of the guiding catheter 20, or the guiding catheter 20 proximally retracted, causing the distal shaft section of the EP device to return to the helically shaped configuration illustrated in FIG. 1. In alternative embodiments (not shown), the helically shaped distal shaft section reversibly collapses to a helical shape with turns having a smaller outer diameter when the distal shaft section is within the guiding catheter lumen 26.

Figure 5:
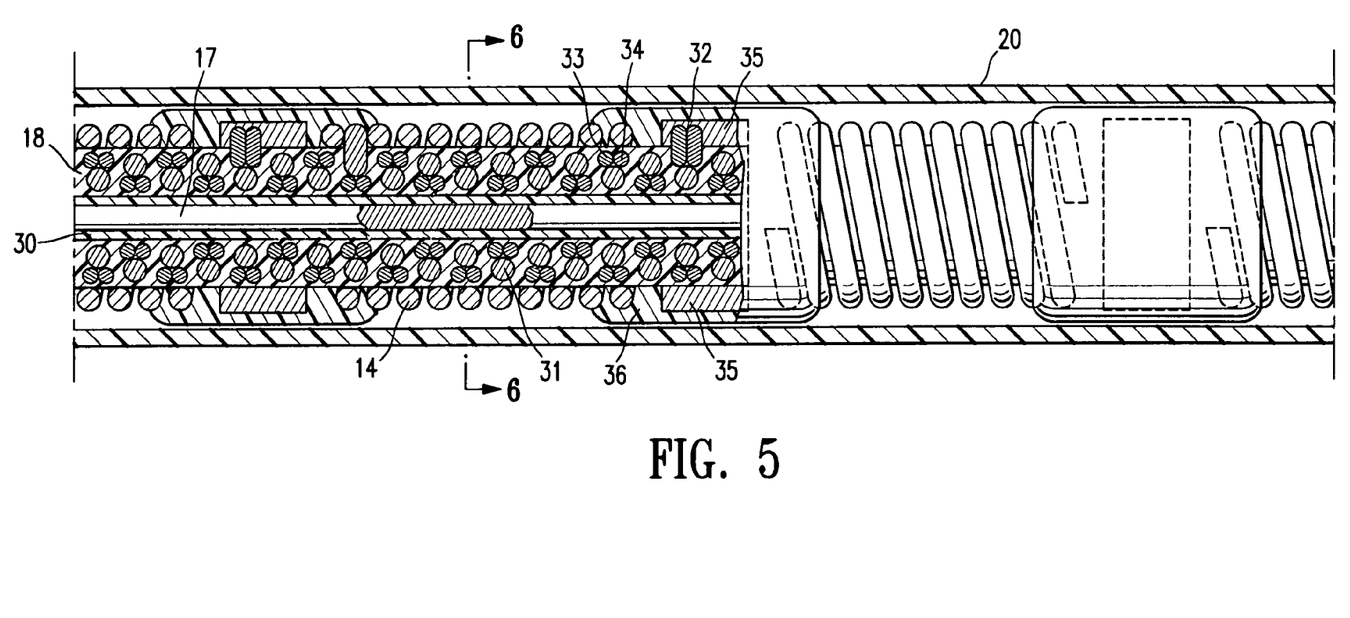
FIG. 5 is an enlarged longitudinal cross-sectional view of the EP device assembly shown in FIG. 3 taken along the lines 5—5, illustrating a portion of the EP device distal shaft section within the guiding catheter.
Figure 6:
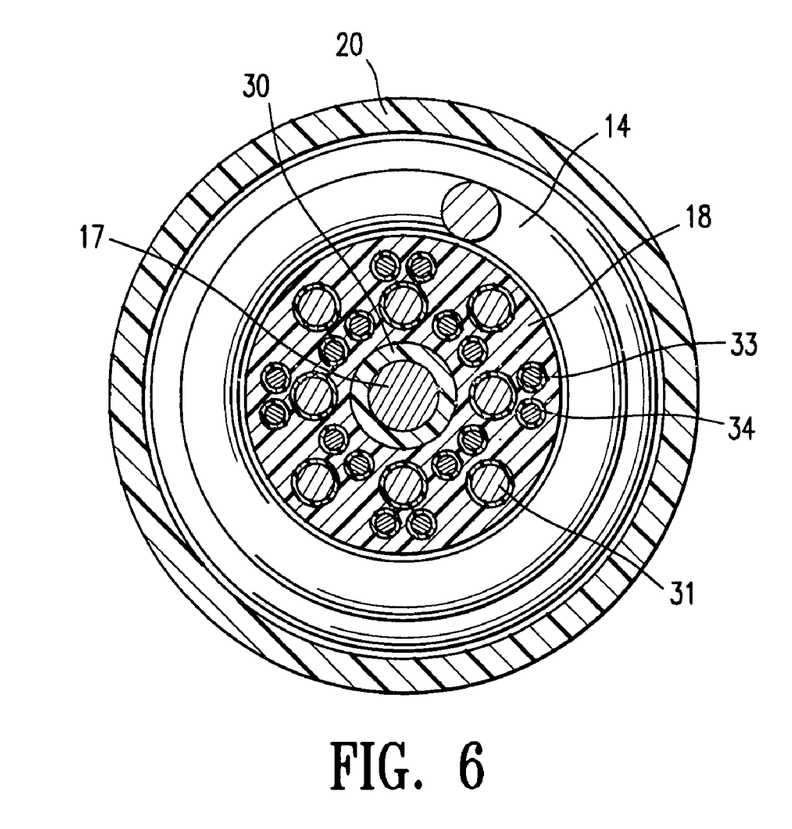
FIG. 6 is a transverse cross sectional view of the EP device assembly shown in FIG. 5, taken along lines 6—6.

In a presently preferred embodiment, the EP device 10 includes a core member 17 having a helically shaped distal section, disposed within the shaft 11. As best illustrated in FIG. 5, showing a longitudinal cross section of the of the EP device shown in FIG. 3, taken along lines 5—5, the shaft 11 comprises a tubular member 18 disposed about the core member 17. The core member 17 extends within the tubular member to the distal end of the device, and the tubular member 18 is helically shaped by the core member therein. FIG. 6 illustrates a transverse cross section of the EP device shown in FIG. 5, taken along lines 6—6.

Figure 4:
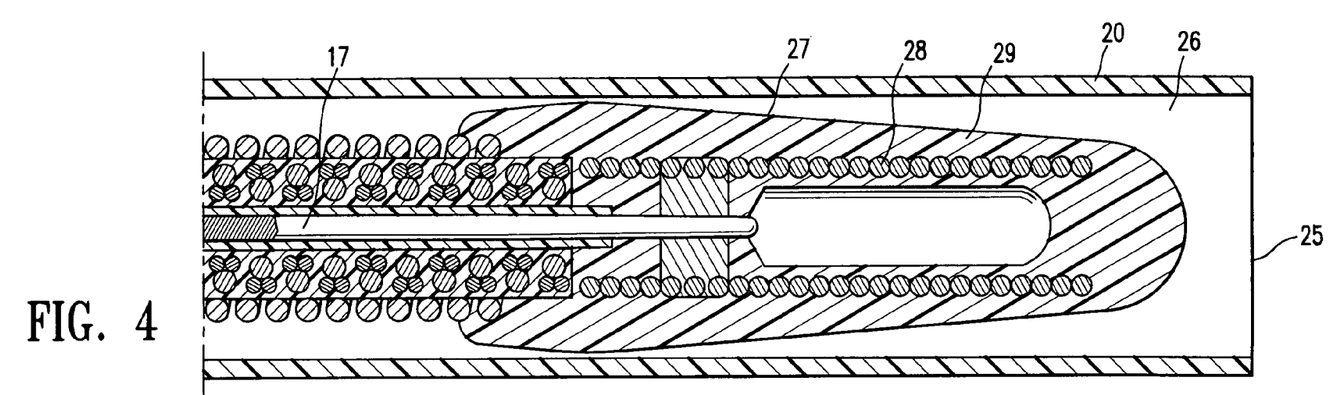
FIG. 4 is an enlarged longitudinal cross-sectional view of the EP device assembly shown in FIG. 3 taken along the lines 4—4, illustrating the EP device distal tip within the guiding catheter.
Figure 7:
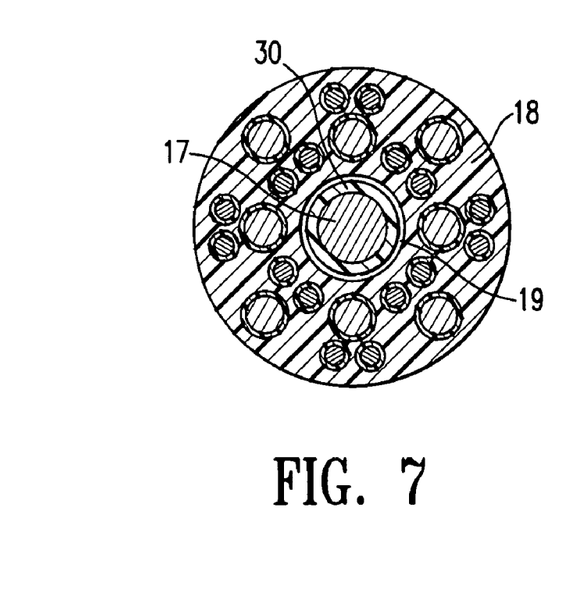
FIG. 7 is a transverse cross sectional view of an alternative embodiment of an EP device assembly embodying features of the invention, having a core wire slidably disposed in a lumen in the device shaft.

The core member 17 is preferably formed of a superelastic material, such as a NiTi alloy, or stainless steel, and has a maximum diameter of about 0.01 inch (0.25 mm) to about 0.018 inch (0.46 mm). The core member 17, and preferably a distal section thereof, may be tapered as shown in FIG. 4, or optionally flattened. In a presently preferred embodiment, the core member has an insulating coating 30, such as a polyester or polyimide coating. The coating 30 is preferably about 0.0005 inch (0.0127 mm) thick. In the embodiment illustrated in FIG. 4, coating 30 extends distally to a point distal to the shaft 11 distal end and proximal to the distal end of core member 17. In the embodiment illustrated in FIGS. 5 and 6, the coating 30 on the core member 17 contacts an inner surface of the tubular member 18. The core member 17 is secured to the tubular member 18 by applying heat to the device to melt and fuse the tubular member to the core member coating. However, a variety of suitable means of securing the core member within the tubular member may be used, such as an adhesive (not shown) between the core member and the tubular member. In an alternative embodiment of the invention illustrated in FIG. 7, the core member 17 is slidably disposed within and removable from a lumen 19 of the tubular member.

As best illustrated in FIG. 4, a flexible coiled tip 27 is provided on the distal end of the EP device 10. The tip 27 has a closed distal end, and includes a flexible coil 28 extending beyond the distal end of the shaft 11 enclosed within a soft coating 29 preferably formed of a polymeric material. In the embodiment illustrated in FIG. 4, the tip 27 has an open center region for increased flexibility. A presently preferred polymeric material for the tip 27 is a fluoropolymer such as THV available from 3M. In the embodiment illustrated in FIG. 4, the core member 17 is secured to the distal end of the coil 28, by suitable material such as gold-tin solder. In another embodiment of the invention, the coil 28 may be omitted, and the distal end of the EP device preferably provided with a soft tip to minimize traumatic engagement with a blood vessel wall.

In the embodiment illustrated in FIGS. 5 and 6, the electrodes 14 comprise helical coils which are electrically connected to insulated electrical conductors 31. In a presently preferred embodiment, the EP device 10 shaft includes thermocouples 32, connected to temperature sensor electrical conductors 33 and 34 (i.e., thermocouple wires). Thermocouples are preferably located between adjacent electrodes on an outer surface of the shaft 11, although they may alternatively be at other locations on the EP device as is conventionally known. A conducting member 35, such as a gold band, covers the thermocouples, and a polymeric jacket 36, preferably formed from THV, covers the conducting member 35 and insulates the thermocouple 32 from noise (e.g. RF noise) present as a result of the energy sent to the electrodes. In the embodiment illustrated in FIG. 5, the electrical conductors 31 and thermocouple wires 33, 34 are braided within the tubular member 18. However, the electrical conductors 31 and thermocouple wires 33, 34 may have a variety of suitable configurations, including braided or wound configurations different from that shown in FIG. 5 or a nonbraided configuration. In an alternative embodiment (not shown), the individually insulated electrical conductors may be within the tubular member lumen 19 or at least in part within an outer jacket of the core member in the embodiment in which the core member is secured to the tubular member. The proximal ends of the electrical conductors 31 and thermocouple wires 33, 34 are electrically connected to individual pins of multi-pin connector 15 (FIG. 1) on the proximal end of the shaft.

Figures 8, 9:
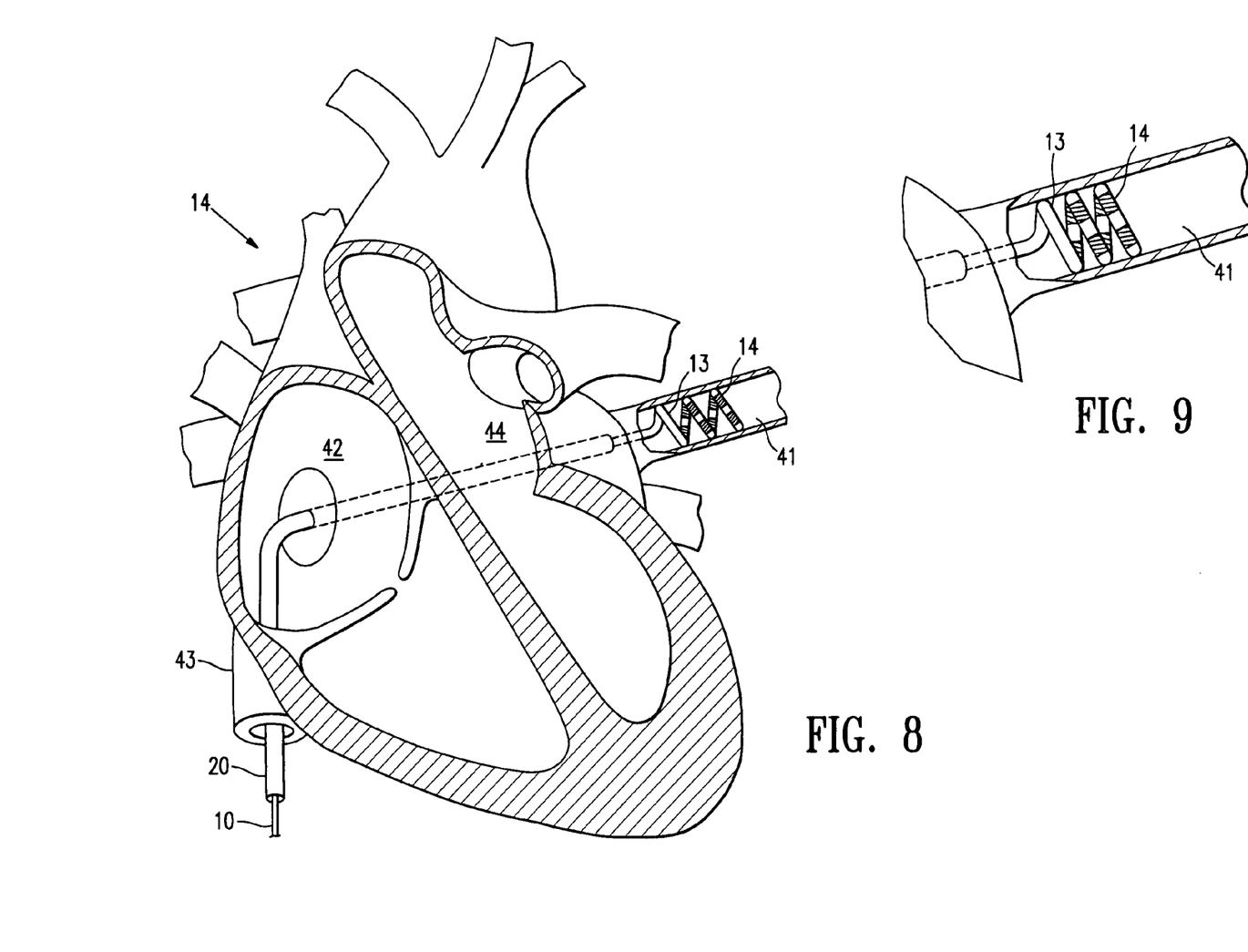
FIG. 8 is an elevational view, partially in section, of a patient's heart and an EP device assembly embodying features of the invention, with the distal end of the EP device transeptally positioned within a pulmonary vein.
FIG. 9 is an elevational view, partially in section, of the EP device assembly of FIG. 8, with the turns of the helically shaped distal shaft section moved closer together in a stacked configuration.

In a method of treating a patient for atrial fibrillation or flutter, the EP device of the invention is used to form a lesion extending around an inner surface of the patient's pulmonary vein. FIG. 8 illustrates an assembly in a patient's heart 40, with the EP device 10 in a pulmonary vein 41. The device 10 is introduced into the patient's vascular system, e.g. the femoral vein, percutaneously or by way of a cutdown, within the guiding catheter 20. The assembly is preferably advanced into the right atrium 42 from the inferior vena cava 43, and positioned in the left atrium 44 traseptally, as illustrated in FIG. 8. The EP device 10 distal section extends out of the port in the distal end of the guiding catheter, so that the helically shaped distal shaft section of the device is positioned within the pulmonary vein 41 of the heart. The pulmonary vein 41 is mapped using electrodes on the device 10, and if a pulmonary vein potential is detected, the electrodes on the distal shaft section are used to form a lesion(s) extending at least in part around the wall defining the pulmonary vein lumen or in the left atrium just outside a pulmonary vein ostium. The position of the lesion is preferably chosen to interrupt the conduction path to the atrium. Alternatively, the lesion may be located to ablate the actual focal origin in the pulmonary vein.

Typically, RF current is delivered to one or two electrodes to perform a first ablation and then to adjacent electrodes, one or two electrodes at a time, until an ablation of desired length is obtained in the body lumen. This reduces the overall power requirements for the assembly. The temperature sensors can be used to detect the temperature of the heart wall between the adjacent electrodes, to control the high frequency energy and determine when the lesions formed by adjacent electrodes overlap to form continuous lesions on the wall defining the body lumen. Additionally, feedback of the temperature data can be used to modulate the power and prevent thrombus in the preferred use, and cooling fluid can also be used. After the ablation, the electrodes 14 can be employed to detect electrical activity to ensure that the ablation has been effective in terminating the fibrillation or flutter. Typically, the procedure is performed for the left and right, superior and inferior pulmonary veins.

The EP device of the invention can be used to form a helical lesion, a closed circular lesion, or a curvilinear segmental (i.e., discontinuous) lesion. For example, in the embodiment illustrated in FIG. 8, a helical lesion on the body lumen wall can be formed by delivering RF energy to the electrodes which as illustrated are contacting the pulmonary vein wall in a helical array. Typically, the helical lesion is formed to extend continuously along the body lumen wall, wherein the individual lesions formed by the longitudinally adjacent electrodes on the shaft overlap to produce one continuous lesion. The helical lesion comprises a spiral having a distal end, and a proximal end longitudinally spaced from the distal end of the spiral. In an alternative embodiment of the invention, the lesion formed extends in a closed circle around the body lumen wall, i.e., a lesion having ends that close together to form a circle. A closed circle lesion can be formed by displacing the device distal section to change the electrode position on the body lumen wall after an initial lesion is formed. For example, in one embodiment of the method of forming a closed circular lesion, a helically shaped lesion is first formed on the body lumen wall, and then the helically shaped distal shaft section of the EP device is rotated or longitudinally displaced proximally or distally, and a second lesion which overlaps with the first lesion is formed, to thereby form at least one closed circular lesion. Alternatively, as illustrated in FIG. 9, the helically shaped distal shaft section of the EP device can be provided with closely spaced, stacked adjacent turns which facilitate the formation of a closed circle lesion.

The spacing between adjacent turns of the helically shaped distal shaft section can be changed by the physician during deployment of the EP device within the body lumen. To increase the spacing between the helical turns of the device, the distal extremity of the EP device is displaced out of the distal end of the guiding catheter so that it is placed in contact with the body lumen wall. The guiding catheter is displaced proximally, while a proximal portion of the EP device is displaced proximally to stretch the turns of the helically shaped distal shaft section apart, so that the portion of the EP device distal shaft section that is still inside the guiding catheter is deployed therefrom with the spacing between the turns increased. Similarly the spacing between the turns may be decreased by retracting the guiding catheter proximally while a proximal portion of the device is displaced distally, to stack the turns of the helically shaped distal shaft section together.

Figures 10, 12:
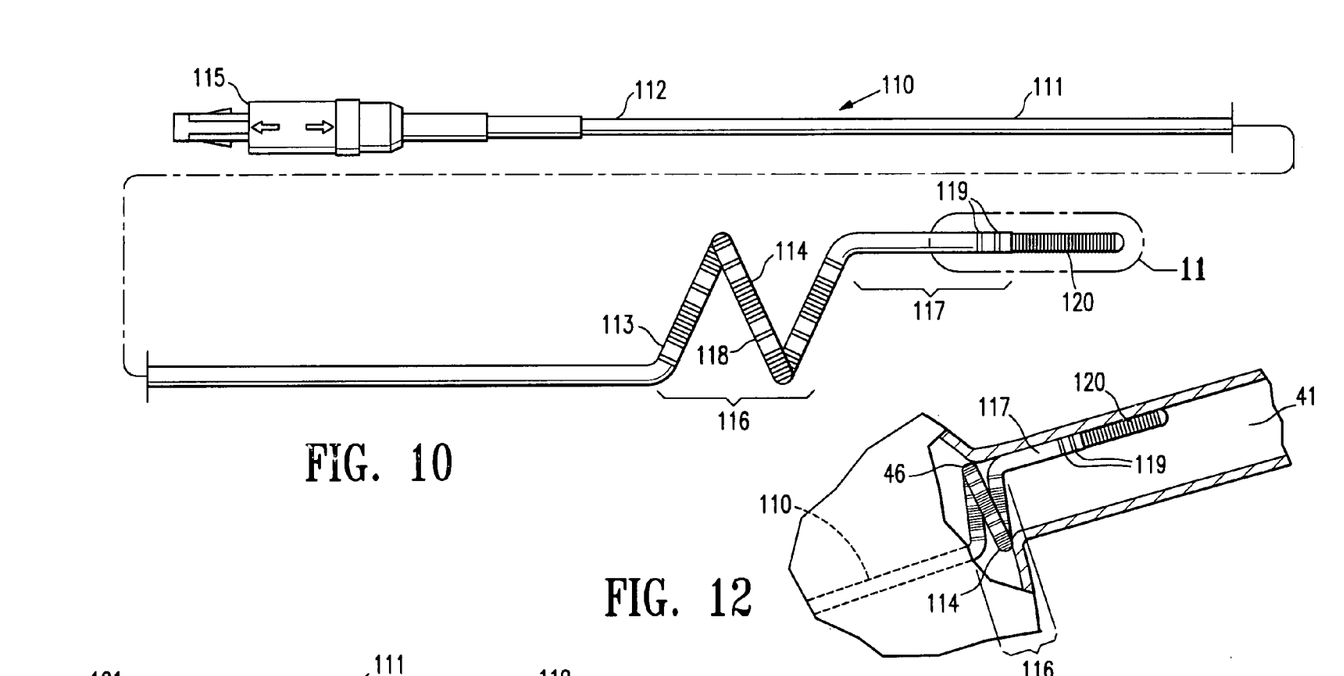
FIG. 10 is an elevational view of an alternative embodiment of an EP device embodying features of the invention comprising a distal shaft section having a proximal portion with a helical shape and a distal portion with a noncoiled shape with a pair or sensing and/or pacing electrodes on the distal portion.
FIG. 12 is an elevational view, partially in section, of the EP device of FIG. 10, positioned in contact with a wall defining a pulmonary vein ostium, with the turns of the helically shaped distal shaft section moved closer together in a stacked configuration.

FIG. 10 illustrates an alternative embodiment of an EP device 110 which embodies features of the invention, generally comprising an elongated shaft 111 having a proximal shaft section 112, a distal shaft section 113, and a plurality of electrodes 114 on the distal shaft section 113. An electrical connector 115 is on the proximal end of the device 110. The distal shaft section 113 comprises a proximal portion 116 with a helical shape having one or more turns, and a distal portion 117 extending from the proximal portion with a noncoiled shape. In the embodiment illustrated in FIG. 10, the noncoiled distal portion 117 has a straight shape with an outer surface aligned or parallel with an outer surface of the proximal shaft section 112. As illustrated in FIG. 10, the noncoiled distal portion 117 has a width about equal to or less than the width of the proximal shaft section 112. Thus, the noncoiled distal portion 117 does not have the enlarged outer diameter formed by the turns of the helically shaped proximal portion 116. The electrodes 114 on the helically shaped proximal portion preferably comprise coiled electrodes, and temperature sensors 118 are located between the coiled electrodes 114, preferably on an outer surface of the shaft, as discussed above in relation to the embodiment of FIG. 1. In a presently preferred embodiment, each electrode 114 has a length of about 3 to about 6 mm. Although 5 electrodes 114 are illustrated in FIG. 10, the number of electrodes 114 may vary, and in a presently preferred embodiment, about 8 electrodes are provided on EP device 110. A pair of sensing electrodes 119 for mapping and/or pacing are on the distal portion 117 of the distal shaft section. In an alternative embodiment (not shown) at least a second pair of sensing and pacing and pacing electrodes 119 may be provided on the shaft proximal to the helically shaped proximal portion 116. The sensing and pacing electrodes are preferably spaced away from the helically coiled section 116, and in one embodiment are about 1 to about 3 cm, preferably about 1.5 to about 2 cm from the helically coiled section. In a presently preferred embodiment, the electrodes 114 on the helically shaped portion 116 are configured for unipolar use during ablation, and bipolar use during sensing. The distal sensing and pacing electrodes 119 are configured for use a bipolar electrodes during sensing and pacing. A flexible coiled tip 120 is secured to the distal end of the distal portion 117, to facilitate guiding the EP device to a desired location within the patient. In a presently preferred embodiment, the tip coil 120 is about 1 to about 3 cm, most preferably about 2 cm in length, and is formed of a radiopaque metal such as platinum.

The turns of the helical proximal section 116 are illustrated in a relaxed configuration in FIG. 10. However, the turns of the helical proximal section 116 can be moved closer together or further apart within the patient by urging the proximal end of the catheter distally or proximally, respectively, with the distal end of the catheter in a stabilized position within the patient and as discussed above in relation to the embodiment of FIG. 1.

Each electrode 114 is spaced apart from one or more adjacent electrodes 114 on the shaft 111, i.e., the electrodes 114 extend discontinuously along the shaft. However, depending on the duration and power level used during an ablation procedure, the lesion(s) formed by electrodes 114 can be discontinuous or alternatively, can be joined together and thus continuous.

In the embodiment illustrated in FIG. 10, the helical proximal portion 116 forms one full 360° loop and half of a second loop. In a presently preferred embodiment, about one full 360° loop is provided, although the number of loops may vary. Because the proximal portion 116 is helical, a proximal section of the 360° loop is longitudinally spaced apart from the distal section thereof which completes the circumference of the loop in the relaxed configuration illustrated in FIG. 10. Consequently, the helical proximal portion forms at least one open or helical 360° loop in the relaxed configuration, and the electrodes 114 thereon form an open or helical 360°, discontinuous loop. The circumference of one 360° loop of the helically proximal portion 116 varies depending on the desired use of the EP device. In a presently preferred embodiment, the circumference of one 360° loop is about 15 mm to about 40 mm, preferably about 15 mm to about 30 mm. Depending on the circumference of the loop and the number and length of the electrodes 114, the electrodes 114 may or may not extend the length of one or more 360° loops. In a presently preferred embodiment, the electrodes 114 extend along the length of at least one 360° loop of the helical proximal portion 116, so that the electrodes can be used to form a lesion which extends in a continuous 360° loop, or a discontinuous, partial segment of a 360° loop. However, in alternative embodiments, the helical proximal portion 116 has a partial loop of less than 360° (not shown), or the electrode number or length is sufficiently small such that the electrodes extend along a length of a partial loop of less than 360° on the helical proximal portion. The circumference of the helical section, i.e., the length of the helical section if it was stretched out to a straight, nonhelical shape, is about 5 to about 40 mm, preferably about 5 to about 20 mm.

Figure 11:
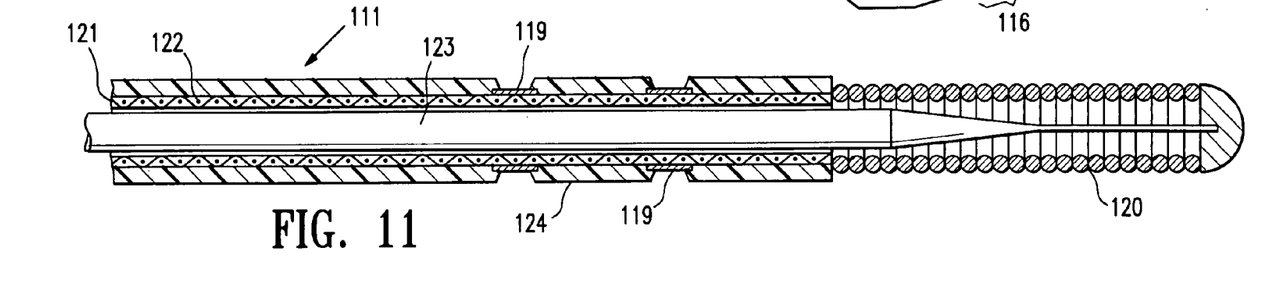
FIG. 11 is a longitudinal cross sectional view of the distal end of the EP device of FIG. 10, taken within circle 11.

FIG. 11 illustrates an enlarged, longitudinal cross sectional view of the distal end of the device 110, taken within circle 11. As illustrated in FIG. 11, the shaft 111 comprises a tubular member 121, having braided electrical conductors 122 in the wall of the tubular member 121, and having a core member 123 in a lumen of the tubular member 121. In the embodiment illustrated in FIG. 11, the core member 123 is secured to the flexible coiled tip 120. An outer layer 124 on an outer surface of the tubular member 121 overlaps the ends of the sensing and pacing electrodes 119.

FIG. 12 illustrates the device 110 with the helically coiled proximal portion 116 of the distal shaft section 113 in position at the ostium 46 of a pulmonary artery which forms the junction between the pulmonary artery and the right atrium of the patient's heart. As illustrated in FIG. 12, the turns of the helically shaped proximal portion 116 are in a stacked configuration after having been moved closer together than the natural relaxed spacing shown in FIG. 10, by distally forcing the catheter against the wall defining the ostium of the pulmonary artery. As a result, the electrodes 114 extend discontinuously, completely around the ostium. High frequency energy is delivered to one or more of the electrodes 114 to form a lesion extending at least in part around the ostium. The lesion can be caused to be a continuous or a discontinuous circular lesion depending on the energy level and the length of time of the ablation, and by rotating the catheter one or more times between delivery of ablation energy to electrodes 114. As illustrated in FIG. 12, the distal portion 117 of the distal shaft section is positioned within the pulmonary vein 41, to allow for mapping and/or pacing from within the pulmonary vein. Thus, the sensing electrodes allow for sensing electrical activity before and after the ablation energy is delivered to electrodes 114, to determine the appropriate location of the device, and whether the lesions formed therefrom sufficiently treated the atrial arrhythmia. Although not illustrated, in one embodiment of performing a medical procedure, the helically shaped proximal portion 116, and the distal portion 117 of the EP device 110 are both positioned within the pulmonary vein 41, similar to the embodiment illustrated in FIGS. 8 and 9.

Figure 13:
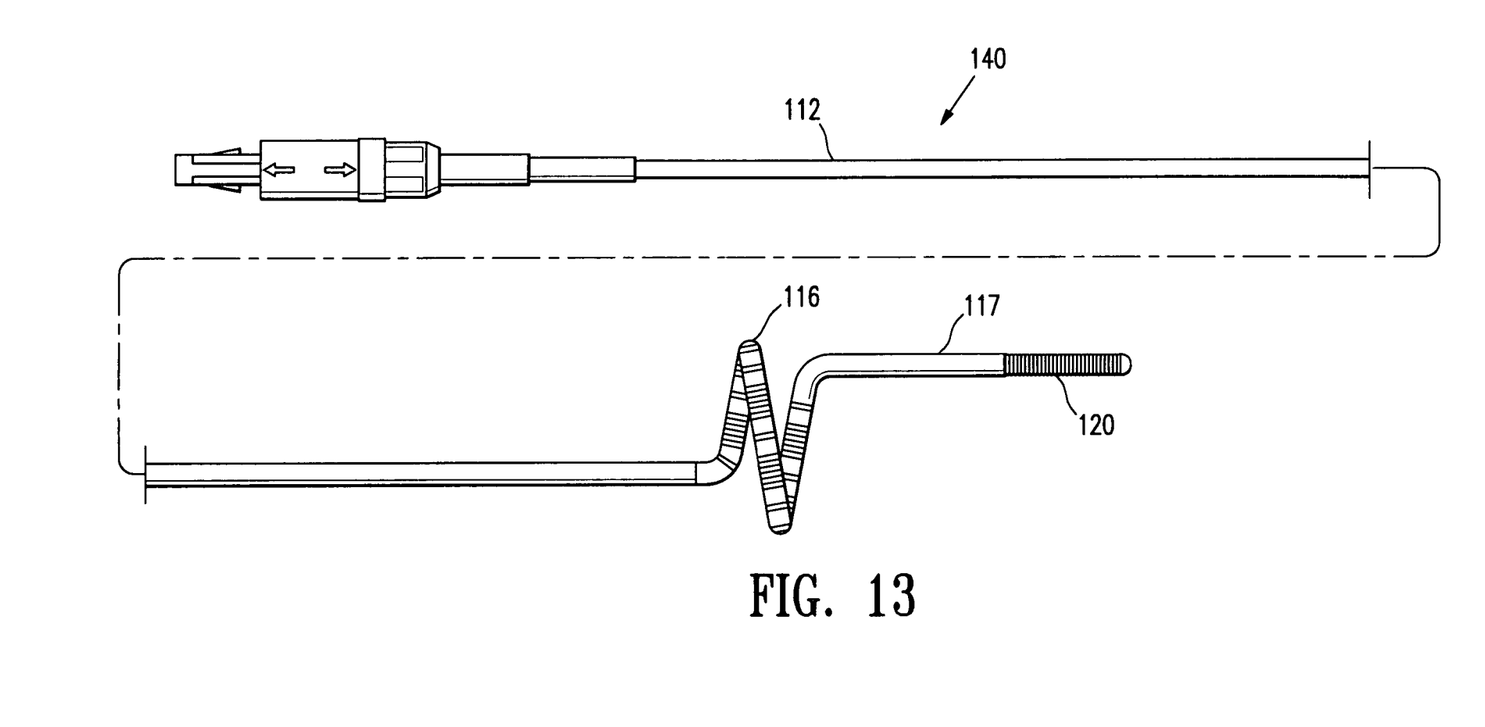
FIG. 13 is an elevational view of an alternative embodiment of an EP device embodying features of the invention comprising a distal shaft section having a proximal portion with a helical shape with one and one quarter turns, and a distal portion with a noncoiled shape.

FIG. 13 illustrates an alternative embodiment of an EP device 140 embodying features of the invention, similar to catheter 110 but with helical proximal portion 116 forming one full 360° loop and one quarter of a second loop, and with no electrodes 119 on the noncoiled distal portion 117. A presently preferred method of using EP device 140 comprises positioning the helical proximal portion 116 just outside a pulmonary vein at the ostium thereof, with the noncoiled distal portion 117 used as an anchoring section within and in contact with the pulmonary vein. The helical proximal portion 116 is pushed against the atrial tissue just outside the pulmonary vein ostium, thereby ensuring good contact with atrial tissue for ablation purposes. Pushing the shaft distally with the helically shaped section braced against the atrial tissue thus collapses the helix and may advance a distal section of the proximal shaft section proximal to the helically shaped distal portion and through the ostium. The electrodes on the helical proximal portion 116 are used to map for pulmonary vein potentials and only a discontinuous, segmental lesion, rather than an entire circumference, continuous lesion, is formed by RF ablation, to barricade the pulmonary vein potentials from exiting the pulmonary vein.

In one method of the invention, the lesion comprises one or more closed circles on the endocardium. However, the lesion may alternatively comprise a discontinuous, partially open circle formed by a plurality of smaller lesions. Additionally, the lesion may be formed by the helical distal shaft section in the noncollapsed configuration to extend helically along a length of the body lumen, or the lesion may be formed by the helical distal shaft section in the collapsed configuration to extend only around the circumference of the body lumen and not helically along a length of the body lumen. Typically, the lesion formed with the EP device 10/110/140 of the present invention has a width of about 2 to about 7 mm, preferably about 3 to about 4 mm. The circumference of the lesion (forming a continuous closed circle, or a discontinuous partially open circle) is about 5 to about 40 mm, preferably about 5 to about 20 mm. A lesion extending only circumferentially around the body lumen and not helically along a length of the body lumen (forming either a continuous closed circle, or a discontinuous partially open circle) has a length of about the thickness of the EP device shaft. A helical lesion extending helically along a length of the body lumen has a length of about to about 5 mm to about 50 mm, preferably about 5 to about 10 mm. Preferably, in the embodiment in which a plurality of continuous, closed circle lesions are formed on the body lumen wall, the lesions are formed near the transition zone between the left atrial tissue and the pulmonary vein tissue.

The EP device 10/110/140 has a total length, including the connector 16, of about 100 cm to about 200 cm, and preferably between 150 and 180, e.g. about 165 cm. The length of the distal shaft section 13/113 having electrodes 14/114 is about 2 cm to about 15 cm, and preferably about 4 to about 8 cm, e.g. about 6 cm. The outer diameter of the distal shaft section of the device is typically about 1.0 mm (3.0 French) to about 2.0 mm (6.0 French), and preferably about 1.3 mm (4 French) to about 1.7 mm (5 French). The maximum outer dimensions of the electrodes are generally about 1.0 mm (3 Fr) to about 1.3 mm (4 Fr), and preferably about 1.22 mm (3.7 Fr). The electrode length is about 2 mm to about 8 mm, and preferably about 4 to about 7 mm, e.g. about 6 mm. The interelectrode spacing is generally about 1 mm to about 3 mm, and preferably about 2 mm. In a presently preferred embodiment, the interelectrode spacing is uniform. However, the electrode spacing may alternatively be nonuniform. In a presently preferred embodiment, about 4 to about 12 individual electrodes are provided on the shaft distal section, however, the device may have larger number of electrodes if the diameter of the distal section is increased to greater than 5 Fr.

Typically, the device is used within the patient's vasculature, although it may also be used to create lesions within other body lumens. The device may be advanced retrogradely through the aorta and left ventricle via a femoral artery access site. As illustrated in FIG. 8, the guiding catheter may have a bent or deflectable distal end. Torquing the proximal section 22 of the guiding catheter, which extends out of the patient during the procedure, will cause the distal section thereof to be rotatably displaced within the body lumen and allow the EP device 10 to be properly positioned.

To the extent not already discussed herein, the EP device components can be formed of conventional materials. The core member 17/123 can be formed of a variety of suitable materials including high spring-back metals, or superelastic metals, or shape memory metals, such as ELGILOY available from Carpenter Technology of Pennsylvania, MP35N, available from SPS Technologies, high tensile strength steel including 304 vacuum-melted steel, and titanium alloys including Ti-GAI-4V, $C_p$ Titanium, and NiTi.

The electrical connector 15 on the proximal end of the device may be a commercially available electrical connector such as Part No. PAB-M08-GLA39J or PAB-M08-TLA39J for an eight pin connector or Part No. PAB-M08-GLA39A for a connector with a greater number of pins, e.g. 9–16. The above connectors are available from Lemo USA, Inc. in Santa Rosa, Calif. Suitable connectors for accessory cables connectable to the above connectors include PRB-M08-GLL65J for eight pin connectors and PRB-M08-GII65A for connectors with more than eight pins. The latter connectors are also available from the same source.

While the invention has been described herein in terms of certain preferred embodiments directed to the detection and treatment of atrial fibrillation and flutter, those skilled in the art will recognize that the invention may be employed in a wide variety of procedures. A variety of modifications and improvements may be made to the present invention without departing from the scope thereof. Moreover, although individual features of embodiments of the invention may be shown or discussed in relation to some of the embodiments and not in others, those skilled in the art will recognize that individual features of one embodiment of the invention can be combined with any or all the features of another embodiment.

What is claimed is:

1. An electrophysiology device configured to be delivered through an inner lumen of a guide catheter to a desired intracorporeal location, comprising:
    a) an elongated shaft which has a proximal shaft section and a distal shaft section, the distal shaft section having a helically shaped proximal portion with at least one turn and a plurality of ablation electrodes and a straight distal portion extending distally from the proximal portion with no ablation electrodes;
    b) a centrally disposed inner core member which extends through the proximal portion of the distal shaft section and at least part of the distal portion, which is formed at least in part of superelastic NiTi alloy, which is in part in the shape of a helical coil to thereby cause the proximal portion of the distal shaft section to take a helical shape with at least one loop having operative transverse dimensions in an unstressed condition and which is in part straight to thereby cause the distal portion to extend straight from the helical coil.

2. The electrophysiology device of claim 1 wherein the loop of the helically shaped proximal portion of the distal shaft section has maximum transverse dimensions larger than transverse dimensions of the inner lumen of the delivery guide catheter.

3. The electrophysiology device of claim 1 wherein a 360° loop of the helically shaped proximal portion of the distal shaft section has a circumference of about 15 to about 40 mm.

4. The electrophysiology device of claim 1 wherein a 360° loop of the helically shaped proximal portion of the distal shaft section has a circumference of about 15 to about 30 mm.

5. The electmphysiology device of claim 1 wherein the helically shaped proximal portion of the distal shaft section has at least one temperature sensor between adjacent ablation electrodes.

6. The electrophysiology device of claim 1 wherein the distal shaft section has a diameter less than about 5 French.

7. The electrophysiology device of claim 1 wherein the distal shaft section has a diameter less than about 4 French.

8. The electrophysiology device of claim 1 wherein the distal shaft section has from 4 to 12 electrodes.

9. The electrophysiology device of claim 1 wherein the electrodes are spaced from each other a distance of about 1 to about 3 mm.

10. The electrophysiology device of claim 1 wherein the distal shaft section has a flexible distal tip coil.

11. The electrophysiology device of claim 10 wherein the core member extends through the flexible distal tip coil and is secured to a distal end thereof.

12. The electrophysiology device of claim 10 wherein the flexible distal tip coil has a length of about 1 to about 3 cm.

13. The electrophysiology device of claim 1 wherein the helically shaped proximal portion of the distal shaft section has at least 4 ablation electrodes.

14. The electrophysiology device of claim 1 wherein the helically shaped proximal portion of the distal shaft section has a thermocouple disposed between adjacent ablation electrodes.

15. The electrophysiology device of claim 1 wherein the straight distal portion of the distal shaft section has a flexible distal tip coil.

16. The electrophysiology device of claim 1 wherein the distal shaft section has at least one sensing electrode.

17. An electrophysiology system comprising:
    a) a guide catheter which has proximal and distal ends, a discharge port in the distal end and an inner lumen extending therein to and in fluid communication with the port in the distal end and which is configured to be advanced within a patient's vasculature to a desired intracorporeal location;
    b) an electrophysiology device which is slidably disposed within the inner lumen of the guiding catheter and which is configured to form a lesion within the patient's heart, comprising:
        i. an elongated shaft which has a proximal shaft section and a distal shaft section, the distal shaft section having a helically shaped proximal portion with at least one loop and a plurality of ablation electrodes and a straight distal portion extending distally from the proximal portion with no ablation electrodes, and
        ii. a centrally disposed, inner core member which extends through the proximal portion of the distal shaft section and at least part of thb distal portion of the distal shaft section, which is formed at least in part of superelastic NiTi alloy, which is in the shape of a helical coil in the proximal portion to thereby cause the proximal portion of the distal shaft section to take a helical shape with at least one loop having operative transverse dimensions in an unstressed condition when the proximal portion extends out of the port in the distal end of the guiding catheter and which has a straight shape in the distal portion to thereby cause the distal portion to be straight.

18. The electrophysiology system of claim 17 wherein the helically shaped proximal portion of the distal shaft section has at least 4 ablation electrodes.

19. The electrophysiology system of claim 17 wherein the helically shaped proximal portion of the distal shaft section has a thermocouple disposed between adjacent ablation electrodes.

20. The electrophysiology system of claim 17 wherein the distal shaft section has at least one sensing electrode.

21. A method of forming a circular or helical lesion within a patient's heart, comprising:
- a. providing a guiding catheter which is configured to be advanced through the patient's vasculature to the desired location within the patient's heart;
- b. providing an electrophysiology device which comprises
  - i) an elongated shaft which has a proximal shaft section and a distal shaft section, the distal shaft section having a helically shaped proximal portion with at least one loop with a plurality of ablation electrodes and a straight distal portion extending distally from the proximal portion with no ablation electrodes; and
  - ii) a centrally disposed, inner core member which extends through the proximal portion and at least part of the distal portion of the distal shaft section, which is formed at least in part of superelastic NiTi alloy and which is in the shape of a helical coil in the proximal portion thereof to thereby cause the proximal portion of the distal shaft section to take a helical shape with a loop thereof having operative transverse dimensions in an unstressed condition and which is straight in the distal portion thereof the cause the distal portion of the distal shaft section to take a straight shape;
- c. disposing the electrophysiology device within the inner lumen of the guiding catheter with the helically shaped proximal portion of the electrophysiology device being constricted within the inner lumen of the guiding catheter to transverse dimensions smaller than the unstressed transverse dimensions;
- d. advancing the electrophysiology device within the inner lumen of the guiding catheter until the helically shaped proximal portion of the electrophysiology device extends out of the distal end of the guiding catheter where the at least one turn of the helically shaped portion self-expands to an operative transverse dimension to fit against the desired intracorporeal location; and
- e. delivering high frequency electrical power to a plurality of electrodes on the proximal portion of the distal shaft section to form a lesion.

22. The method of claim 21 wherein the lesion formed is less than about 7 mm in width.

23. The method of claim 21 wherein the lesion formed is less than about 4 mm in width.

24. The method of claim 21 wherein the helically shaped proximal portion of the distal shaft section has at least 4 ablation electrodes.

25. The method of claim 21 wherein the helically shaped proximal portion of the distal shaft section has a thermocouple disposed between adjacent ablation electrodes configured to detect temperature during ablation.

26. The method of claim 21 wherein the distal shaft section has at least one sensing electrode.

* * * * *